US008692019B2

(12) United States Patent
Tearney et al.

(10) Patent No.: US 8,692,019 B2
(45) Date of Patent: Apr. 8, 2014

(54) ELECTROCHEMICAL CO-PRODUCTION OF CHEMICALS UTILIZING A HALIDE SALT

(71) Applicant: Liquid Light, Inc., Monmouth Junction, NJ (US)

(72) Inventors: Kyle Tearney, Washington, DC (US); Jerry J. Kaczur, North Miami Beach, FL (US)

(73) Assignee: Liquid Light, Inc., Monmouth Junction, NJ (US)

( * ) Notice: Subject to any disclaimer, the term of this patent is extended or adjusted under 35 U.S.C. 154(b) by 0 days.

(21) Appl. No.: 13/724,807

(22) Filed: Dec. 21, 2012

(65) Prior Publication Data

US 2013/0137898 A1 May 30, 2013

Related U.S. Application Data

(60) Provisional application No. 61/703,231, filed on Sep. 19, 2012, provisional application No. 61/720,670, filed on Oct. 31, 2012, provisional application No. 61/675,938, filed on Jul. 26, 2012, provisional application No. 61/703,231, filed on Sep. 19, 2012, provisional application No. 61/703,229, filed on Sep. 19, 2012, provisional application No. 61/703,158, filed on Sep. 19, 2012, provisional application No. 61/703,175, filed on Sep. 19, 2012, provisional application No. 61/703,232, filed on Sep. 19, 2012, provisional application No. 61/703,234, filed on Sep. 19, 2012, provisional application No. 61/703,238, filed on Sep. 19, 2012, provisional application No. 61/703,187, filed on Sep. 19, 2012.

(51) Int. Cl.
*C07C 55/07* (2006.01)
*C07C 19/075* (2006.01)

(52) U.S. Cl.
USPC .......................................... 562/597; 570/252

(58) Field of Classification Search
CPC ...................................................... C07C 51/15
See application file for complete search history.

(56) References Cited

U.S. PATENT DOCUMENTS

| | | |
|---|---|---|
| 3,019,256 A | 1/1962 | Dunn |
| 3,293,292 A | 12/1966 | Olivier et al. |
| 3,326,998 A | 6/1967 | Reusser et al. |
| 3,341,615 A | 9/1967 | Wulf et al. |
| 3,341,616 A | 9/1967 | Vives |
| 3,352,935 A | 11/1967 | Mahan |
| 3,361,653 A | 1/1968 | Miller |
| 3,401,100 A | 9/1968 | Macklin |
| 3,492,209 A | 1/1970 | Miller |
| 3,560,354 A | 2/1971 | Young |
| 3,607,962 A | 9/1971 | Krekeler et al. |
| 3,636,159 A | 1/1972 | Solomon |
| 3,720,591 A * | 3/1973 | Skarlos ........................ 562/597 |
| 3,745,180 A | 7/1973 | Rennie |
| 3,764,492 A | 10/1973 | Baizer et al. |
| 3,779,875 A | 12/1973 | Michelet |
| 4,072,583 A | 2/1978 | Hallcher et al. |
| 4,087,470 A | 5/1978 | Suzuki |
| 4,088,682 A | 5/1978 | Jordan |
| 4,162,948 A | 7/1979 | Yagii et al. |
| 4,219,392 A | 8/1980 | Halmann |
| 4,245,114 A | 1/1981 | Peltzman |
| 4,256,550 A | 3/1981 | Niinobe et al. |
| 4,343,690 A | 8/1982 | de Nora |
| 4,381,978 A | 5/1983 | Gratzel et al. |
| 4,450,055 A | 5/1984 | Stafford |
| 4,476,003 A | 10/1984 | Frank et al. |
| 4,523,981 A | 6/1985 | Ang et al. |
| 4,547,271 A | 10/1985 | Bharucha et al. |
| 4,595,465 A | 6/1986 | Ang et al. |
| 4,608,132 A | 8/1986 | Sammells |
| 4,608,133 A | 8/1986 | Morduchowitz et al. |
| 4,619,743 A | 10/1986 | Cook |
| 4,661,422 A | 4/1987 | Marianowski et al. |
| 4,673,473 A | 6/1987 | Ang et al. |
| 4,702,973 A | 10/1987 | Marianowski |
| 4,732,655 A * | 3/1988 | Morduchowitz et al. ..... 205/453 |
| 4,902,828 A | 2/1990 | Wickenhaeuser et al. |
| 4,968,393 A | 11/1990 | Mazur et al. |
| 5,074,974 A | 12/1991 | Toomey, Jr. |
| 5,107,040 A | 4/1992 | Repman et al. |
| 5,155,256 A | 10/1992 | Chapman |
| 5,198,086 A | 3/1993 | Chlanda et al. |
| 5,290,404 A | 3/1994 | Toomey |
| 5,412,150 A | 5/1995 | Wessel |
| 5,443,804 A | 8/1995 | Parker et al. |
| 5,514,492 A | 5/1996 | Marincic et al. |
| 5,654,493 A | 8/1997 | Wessel |

(Continued)

FOREIGN PATENT DOCUMENTS

| | | |
|---|---|---|
| CA | 1146120 A1 | 5/1983 |
| CA | 1272161 A1 | 7/1990 |

(Continued)

OTHER PUBLICATIONS

Zaragoza Dorwald, Side Reactions in Organic Synthesis, 2005, WILEY-VCH Verlag GmbH & Co. KGaA, Weinheim, Preface. p. IX.*

(Continued)

*Primary Examiner* — Paula A Zucker
(74) *Attorney, Agent, or Firm* — Suiter Swantz pc llo

(57) ABSTRACT

The present disclosure includes a system and method for co-producing a first product and a second product. The system may include a first electrochemical cell, at least one second reactor, and an acidification chamber. The method and system for co-producing a first product and a second product may include co-producing a carboxylic acid and at least one of an alkene, alkyne, aldehyde, ketone, or an alcohol while employing a recycled halide salt.

27 Claims, 7 Drawing Sheets

(56) References Cited

U.S. PATENT DOCUMENTS

| | | | |
|---|---|---|---|
| 5,804,045 | A | 9/1998 | Orillon et al. |
| 6,024,935 | A | 2/2000 | Mills et al. |
| 6,251,256 | B1 | 6/2001 | Blay et al. |
| 6,380,446 | B1 | 4/2002 | Drew et al. |
| 6,465,699 | B1 | 10/2002 | Grosso |
| 6,777,571 | B2 | 8/2004 | Chaturvedi et al. |
| 7,462,752 | B2 | 12/2008 | Fong et al. |
| 7,883,610 | B2 | 2/2011 | Monzyk et al. |
| 8,313,634 | B2 | 11/2012 | Bocarsly et al. |
| 2001/0026884 | A1 | 10/2001 | Appleby et al. |
| 2002/0022753 | A1 | 2/2002 | Drew et al. |
| 2006/0102468 | A1 | 5/2006 | Monzyk et al. |
| 2007/0004023 | A1 | 1/2007 | Trachtenberg et al. |
| 2007/0012577 | A1 | 1/2007 | Bulan et al. |
| 2007/0224479 | A1 | 9/2007 | Tadokoro et al. |
| 2008/0223727 | A1 | 9/2008 | Oloman et al. |
| 2008/0248350 | A1 | 10/2008 | Little et al. |
| 2008/0283411 | A1 | 11/2008 | Eastman et al. |
| 2008/0286643 | A1 | 11/2008 | Iwasaki |
| 2008/0296146 | A1 | 12/2008 | Toulhoat et al. |
| 2008/0314758 | A1 | 12/2008 | Grosso |
| 2009/0014336 | A1 | 1/2009 | Olah et al. |
| 2009/0030240 | A1 | 1/2009 | Olah et al. |
| 2010/0187123 | A1 | 7/2010 | Bocarsly et al. |
| 2010/0187125 | A1 | 7/2010 | Sandoval et al. |
| 2010/0191024 | A1 | 7/2010 | Uenveren et al. |
| 2010/0196800 | A1 | 8/2010 | Markoski et al. |
| 2010/0248042 | A1 | 9/2010 | Nakagawa et al. |
| 2010/0270167 | A1 | 10/2010 | McFarland |
| 2010/0330435 | A1 | 12/2010 | Nemeth et al. |
| 2011/0083968 | A1 | 4/2011 | Gilliam et al. |
| 2011/0114501 | A1 | 5/2011 | Teamey et al. |
| 2011/0114502 | A1 | 5/2011 | Cole et al. |
| 2011/0114503 | A1 | 5/2011 | Sivasankar et al. |
| 2011/0114504 | A1 | 5/2011 | Sivasankar et al. |
| 2011/0143929 | A1 | 6/2011 | Sato et al. |
| 2011/0186441 | A1 | 8/2011 | LaFrancois et al. |
| 2011/0226632 | A1 | 9/2011 | Cole et al. |
| 2011/0237830 | A1 | 9/2011 | Masel |
| 2012/0004448 | A1 | 1/2012 | Bhattacharyya et al. |
| 2012/0004449 | A1 | 1/2012 | Bhattacharyya |
| 2012/0004454 | A1 | 1/2012 | Bhattacharyya et al. |
| 2012/0018311 | A1 | 1/2012 | Yotsuhashi et al. |
| 2012/0043301 | A1 | 2/2012 | Arvin et al. |
| 2012/0215034 | A1 | 8/2012 | McFarland |
| 2012/0228147 | A1 | 9/2012 | Sivasankar et al. |
| 2012/0292196 | A1 | 11/2012 | Albrecht et al. |
| 2012/0295172 | A1 | 11/2012 | Peled et al. |
| 2012/0298522 | A1 | 11/2012 | Shipchandler et al. |
| 2012/0329657 | A1 | 12/2012 | Eastman et al. |
| 2013/0062216 | A1 | 3/2013 | Yotsuhashi et al. |
| 2013/0098772 | A1 | 4/2013 | Bocarsly et al. |
| 2013/0105304 | A1 | 5/2013 | Kaczur et al. |
| 2013/0105330 | A1 | 5/2013 | Teamey et al. |
| 2013/0118911 | A1 | 5/2013 | Sivasankar et al. |
| 2013/0134048 | A1 | 5/2013 | Teamey et al. |
| 2013/0134049 | A1 | 5/2013 | Teamey et al. |
| 2013/0140187 | A1 | 6/2013 | Teamey et al. |
| 2013/0180863 | A1 | 7/2013 | Kaczur et al. |

FOREIGN PATENT DOCUMENTS

| | | |
|---|---|---|
| CA | 2043256 A1 | 12/1991 |
| CA | 2391938 A1 | 5/2001 |
| DE | 1047765 A | 12/1958 |
| DE | 2301032 A | 7/1974 |
| FR | 853643 | 3/1940 |
| GB | 1096847 A | 12/1967 |
| GB | 1584524 A | 4/1977 |
| GB | 2038335 A | 7/1980 |
| GB | 2312218 A | 10/1997 |
| JP | 64-015388 | 1/1989 |
| WO | WO 9724320 A1 | 7/1997 |
| WO | WO 0015586 A1 | 3/2000 |
| WO | WO0138275 A1 | 5/2001 |
| WO | WO 2004067673 A1 | 8/2004 |
| WO | 2007041872 A1 | 4/2007 |
| WO | WO 2007041872 A1 | 4/2007 |
| WO | WO 2012046362 A1 | 4/2012 |

OTHER PUBLICATIONS

Liansheng et al, Journal of South Central University Technology, Electrode Selection of Electrolysis with Membrane for Sodium Tungstate Solution, 1999, 6(2), pp. 107-110.*

Green et al., "Vapor-Liquid Equilibria of Formaldehyde-Methanol-Water", Industrial and Engineering Chemistry (Jan. 1955), vol. 47, No. 1, pp. 103-109.

Shibata et al., "Electrochemical Synthesis of Urea at Gas-Diffusion Electrodes Part VI. Simultaneous Reduction of Carbon Dioxide and Nitrite Ions with Various Metallophthalocyanine Catalysts". J. of Electroanalytical Chemistry (no month, 2001), vol. 507, pp. 177-184.

Jaaskelainen and Haukka, The Use of Carbon Dioxide in Ruthenium Carbonyl Catalyzed 1-hexene Hydroformylation Promoted by Alkali Metal and Alkaline Earth Salts, Applied Catalysis A: General, 247, 95-100 (2003).

Heldebrant et al., "Reversible Zwitterionic Liquids, The Reaction of Alkanol Guanidines, Alkanol Amidines, and Diamines wih $CO_2$", Green Chem. (mo month, 2010), vol. 12, pp. 713-721.

Perez et al., "Activation of Carbon Dioxide by Bicyclic Amidines", J. Org. Chem. (no month, 2004), vol. 69, pp. 8005-8011.

Eggins, Brown, McNeill, and Grimshaw, Carbon Dioxide Fixation by Electrochemical Reduction in Water to Oxalate and Glyoxylate, Tetrahedron Letters vol. 29, No. 8, pp. 945-948, 1988, Pergamon Journals Ltd., Printed in Great Britain.

M. Alvarez-Guerra et al., Conversion of carbon dioxide into formate using a continuous electrochemical reduction process in a lead cathode, Chem. Eng. J. (2012), http://dx.doi.org/10.1016/j.cej.2012.06.099.

Afroza Begum, Electrochemical CO2 Reduction, Thesis, 2011, University of Newfoundland, http://collections.mun.ca/cdm4/document.php?CISOROOT=/theses5&CISOPTR=14718&REC=7.

Satoshi Kaneco, Kenji Iiba, Nobu-Hide Hiei, Kiyohisa Ohta, Takayuki Mizuno, and Tohru Suzuki, Electrochemical reduction of carbon dioxide to ethylene with high Faradaic efficiency at a Cu electrode in CsOH/methanol, Electrochimica Acta 44 (1999) 4701-4706.

Keith Scott, A Preliminary Investigation of the Simultaneous Anodic and Cathodic Production of Glyoxylic Acid, Electrochimica Acta, vol. 36, No. 9, pp. 1447-1452, 1991, Printed in Great Britain.

B. Eneau-Innocent et al., Electroreduction of carbon dioxide at a lead electrode in propylene carbonate: A spectroscopic study, Applied Catalysis B: Environmental 98 (2010) 65-71.

Kotaro Ogura et al., Selective Conversion of CO2 to Ethylene by the Electrolysis at a Three-Phase (Gas/Liquid/Solid) Interface in an Acidic Solution Containing Cupric Ions, Fuel Chemistry Division Preprints 2003, 48(1), 264.

S. Gambino and G. Silvestri, On the electrochemical reduction of carbon dioxide and ethylene, Tetrahedron Letters No. 32, pp. 3025-3028, 1973, Pergamon Press, Printed in Great Britain.

K.S. Udupa, G.S. Subramanian, and H.V.K. Udupa, The electrolytic reduction of carbon dioxide to formic acid, Electrochimica Acta, 1971, vol. 16, pp. 1593 to 1598, Pergamon Press, Printed in Northern Ireland.

Seshadri et al, "A new homogeneous catalyst for the reduction of carbon dioxide to methanol at low overpotential," Journal of Electroanalytical Chemistry, 372 (1994) 145-150.

Scibioh et al, "Electrochemical Reductin of Carbon Dioxide: A Status Report," Proc. Indian Natn Science Acad., 70, A, No. 3, May 2004, pp. 407-762.

Fukaya et al., "Electrochemical Reduction of Carbon Dioxide to Formate Catalyzed by Rh(bpy)3Cl3", Kagaku Gijutsu Kenkyusho Hokoku (no month, 1986), vol. 81, No. 5, pp. 255-258. 1-page abstract only.

Li et al., "the Electro-Reduction of Carbon Dioxide in a Continuous Reactor", J. of Applied Electrochemistry (no month, 2005), vol. 35, pp. 955-965.

(56) References Cited

OTHER PUBLICATIONS

Kaneco et al., "Electrochemical Reduction of Carbon Dioxide to Ethylene with High Faradaic Efficiency at a Cu Electrode in CsOH/Methanol", Electrochimica Acta (no month, 1999), vol. 44, pp. 4701-4706.

Kaneco et al., "Electrochemical Conversion of Carbon Dioxide to Formic Acid on Pb in KOH/Methanol Electrolyte at Ambient Temperature and Pressure", Energy (no month, 1998), vol. 23, No. 12, pp. 1107-1112.

Yuan et al., "Electrochemical Activation of Carbon Dioxide for Synthesis of Dimethyl Carbonate in an Ionic Liquid", Electrochimica Acta (no month, 2009), vol. 54, pp. 2912-2915.

U.S. Appl. No. 13/724,647, filed Dec. 21, 2012; Office Action mailed Oct. 17, 2013.

U.S. Appl. No. 13/787,481, filed Mar. 6, 2013; Office Action mailed Sep. 13, 2013.

U.S. Appl. No. 13/724,082, filed Dec. 21, 2012; Office Action mailed Aug. 12, 2013.

U.S. Appl. No. 13/724,522, filed Dec. 21, 2012; Office Action mailed Oct. 1, 2013.

U.S. Appl. No. 13/724,885, filed Dec. 21, 2012; Office Action mailed Aug. 21, 2013.

U.S. Appl. No. 13/724,231, filed Dec. 21, 2012; Office Action mailed Aug. 20, 2013.

Czerwinski et al, "Adsorption Study of CO2 on Reticulated vitreous carbon (RVC) covered with platinum," Analytical Letters, vol. 18, Issue 14 (1985), pp. 1717-1722.

Hammouche et al, Chemical Catalysis of Electrochemical Reactions. Homogeneous Catalysis of the Electrochemical Reduction of Carbon Dioxide by Iron ("0") Porphyrins. Role of the Addition of Magnesium Cations. J. Am. Chem. Soc. 1991, 113, 8455-8466.

Hossain et al., Palladium and Cobalt Complexes of Substituted Quinoline, Bipyridine and Phenanthroline as Catalysts for Electrochemical Reduction of Carbon Dioxide, Electrochimica Acta (no month, 1997), vol. 42, No. 16, pp. 2577-2785.

Scibioh et al., "Electrochemical Reduction of Carbon Dioxide: A Status Report", Proc Indian Natn Sci Acad (May 2004), vol. 70, A, No. 3, pp. 407-462.

Seshardi G., Lin C., Bocarsly A.B., A new homogeneous electrocatalyst for the reduction of carbon dioxide to methanol at low overpotential, Journal of Electroanalytical Chemistry, 1994, 372, pp. 145-150.

Seshadri et al., "A new homogeneous electrocatalyst for the reduction of carbon dioxide to methanol at low overpotential", Journal of Electroanalytical Chemistry and Interfacial Electro Chemistry, Elsevier, Amsterdam, NL, vol. 372, No. 1-2, Jul. 8, 1994, pp. 145-150.

Hossain et al., "Palladium and cobalt complexes of substituted quinoline, bipyridine and phenanthroline as catalysts for electrochemical reduction of carbon dioxide", Electrochimica Acta, Elsevier Science Publishers, vol. 42, No. 16, Jan. 1, 1997, pp. 2577-2585.

Fisher et al., "Electrocatalytic reduction of carbon dioxide by using macrocycles of nickel and cobalt", Journal of the American Chemical Society, vol. 102, No. 24, Sep. 1, 1980, pp. 7361-7363.

Ishida et al., Selective Formation of HC00—In the Electrochemical CO2 Reduction Catalyzed by URU(BPY)2(CO)2 3/4 2+ (BPY = 2, 2'-Bipyridine), Journal of the Chemical Society, Chemical Communications, Chemical Society, Letchworth, GB, Jan. 1, 1987, pp. 131-132.

Zhao et al., "Electrochemical reduction of supercritical carbon dioxide in ionic liquid 1-n-butyl-3-methylimidazolium hexafluorophosphate", Journal of Supercritical Fluids, PRA Press, US, vol. 32, No. 1-3, Dec. 1, 2004, pp. 287-291.

Seshadri et al., A New Homogeneous Electrocatalyst for the Reduction of Carbon Dioxide to Methanol at Low Overpotential, Journal of Electroanalytical Chemistry, 372 (1994), 145-50.

Green et al., Vapor-Liquid Equilibria of Formaldehyde-Methanol-Water, Industrial and Engineering Chemistry (Jan. 1955), vol. 47, No. 1, pp. 103-109.

Scibioh et al., Electrochemical Reduction of Carbon Dioxide: A Status Report, Proc Indian Natn Sci Acad (May 2004), vol. 70, A, No. 3, pp. 407-462.

Gennaro et al., Homogeneous Electron Transfer Catalysis of the Electrochemical Reduction of Carbon Dioxide. Do Aromatic Anion Radicals React in an Outer-Sphere Manner?, J. Am. Chem. Soc. (no month, 1996), vol. 118, pp. 7190-7196.

Perez et al., Activation of Carbon Dioxide by Bicyclic Amidines, J. Org. Chem. (no month, 2004), vol. 69, pp. 8005-8011.

Zaragoza Dorwald, Side Reactions in Organic Synthesis, 2005, WILEY-VCH Verlag GmbH & Co. KGaA, Weinheim, Preface. Pg. IX.

Mahmood et al., Use of Gas-Diffusion Electrodes for High-Rate Electrochemical Reduction of Carbon Dioxide. II. Reduction at Metal Phthalocyanine-Impregnated Electrodes, J. of Appl. Electrochem. (no month, 1987), vol. 17, pp. 1223-1227.

Tanno et al., Electrolysis of Iodine Solution in a New Sodium Bicarbonate-Iodine Hybrid Cycle, International Journal of Hydrogen Energy (no month, 1984), vol. 9, No. 10, pp. 841-848.

* cited by examiner

US 8,692,019 B2

ELECTROCHEMICAL CO-PRODUCTION OF CHEMICALS UTILIZING A HALIDE SALT

CROSS-REFERENCE TO RELATED APPLICATIONS

The present application claims the benefit under 35 U.S.C. §119(e) of U.S. Provisional Application Ser. No. 61/720,670 filed Oct. 31, 2012, U.S. Provisional Application Ser. No. 61/703,231 filed Sep. 19, 2012 and U.S. Provisional Application Ser. No. 61/675,938 filed Jul. 26, 2012. Said U.S. Provisional Application Ser. No. 61/720,670 filed Oct. 31, 2012, U.S. Provisional Application Ser. No. 61/703,231 filed Sep. 19, 2012 and U.S. Provisional Application Ser. No. 61/675,938 filed Jul. 26, 2012 are incorporated by reference in their entireties.

The present application also claims the benefit under 35 U.S.C. §119(e) of U.S. Provisional Application Ser. No. 61/703,229 filed Sep. 19, 2012, U.S. Provisional Application Ser. No. 61/703,158 filed Sep. 19, 2012, U.S. Provisional Application Ser. No. 61/703,175 filed Sep. 19, 2012, U.S. Provisional Application Ser. No. 61/703,232 filed Sep. 19, 2012, U.S. Provisional Application Ser. No. 61/703,234 filed Sep. 19, 2012, U.S. Provisional Application Ser. No. 61/703,238 filed Sep. 19, 2012, U.S. Provisional Application Ser. No. 61/703,187 filed Sep. 19, 2012. The U.S. Provisional Application Ser. No. 61/703,229 filed Sep. 19, 2012, U.S. Provisional Application Ser. No. 61/703,158 filed Sep. 19, 2012, U.S. Provisional Application Ser. No. 61/703,175 filed Sep. 19, 2012, U.S. Provisional Application Ser. No. 61/703,232 filed Sep. 19, 2012, United States Provisional Application Ser. No. 61/703,234 filed Sep. 19, 2012, U.S. Provisional Application Ser. No. 61/703,238 filed Sep. 19, 2012 and U.S. Provisional Application Ser. No. 61/703,187 filed Sep. 19, 2012 are hereby incorporated by reference in their entireties.

The present application incorporates by reference co-pending U.S. patent application Ser. No. 13/724,339 filed on Dec. 21, 2012, U.S. patent application Ser. No. 13/724,878 filed on Dec. 21, 2012, U.S. patent application Ser. No. 13/724,647 filed on Dec. 21, 2012, U.S. patent application Ser. No. 13/724,231 filed on Dec. 21, 2012, U.S. patent application Ser. No. 13/724,996 filed on Dec. 21, 2012 U.S. patent application Ser. No. 13/724,719 filed on Dec. 21, 2012, U.S. patent application Ser. No. 13/724,082 filed on Dec. 21, 2012, and U.S. patent application Ser. No. 13/724,768 filed on Dec. 21, 2012, now U.S. Pat. No. 8,444,844 in their entireties.

TECHNICAL FIELD

The present disclosure generally relates to the field of electrochemical reactions, and more particularly to methods and/or systems for electrochemical co-production of a carboxylic acid employing a recycled reactant.

BACKGROUND

The combustion of fossil fuels in activities such as electricity generation, transportation, and manufacturing produces billions of tons of carbon dioxide annually. Research since the 1970s indicates increasing concentrations of carbon dioxide in the atmosphere may be responsible for altering the Earth's climate, changing the pH of the ocean and other potentially damaging effects. Countries around the world, including the United States, are seeking ways to mitigate emissions of carbon dioxide.

A mechanism for mitigating emissions is to convert carbon dioxide into economically valuable materials such as fuels and industrial chemicals. If the carbon dioxide is converted using energy from renewable sources, both mitigation of carbon dioxide emissions and conversion of renewable energy into a chemical form that can be stored for later use will be possible.

SUMMARY

The present disclosure includes a system and method for co-producing a first product and a second product. The system may include a first electrochemical cell, at least one second reactor, and an acidification chamber. The method and system for co-producing a first product and a second product may include co-producing a carboxylic acid and at least one of an alkene, alkyne, aldehyde, ketone, or an alcohol while employing a recycled halide salt.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

The systems and methods of the present disclosure may include an electrochemical cell that includes an input of a recycled reactant to co-produce valuable products at both the cathode and anode sides of the electrochemical cell. In one embodiment, carbon dioxide may be reduced in a catholyte region of the electrochemical cell to a carboxylate, and a halide salt is oxidized in an anode region of the electrochemical cell to a halogen. The carboxylate may be fed into an acidification chamber along with a hydrogen halide to form a carboxylic acid and the halide salt. The halide salt is then recycled to the anode region of the electrochemical cell. The halogen produced in the anode compartment is subsequently fed to a second reactor along with an alkane, alkene, aromatic, or other organic compound to produce a halogenated compound and a hydrogen halide. The halogenated compound may be further treated in a third reactor to produce an alkene, alkyne, aldehyde, ketone, or an alcohol. The third reactor also produces additional hydrogen halide, which may be fed to the acidification chamber. In one embodiment, the method and system of the present disclosure may use a source of carbon dioxide, an alkane, alkene, aromatic or other organic compound in order to efficiently produce an alkene, alkyne, aldehyde, ketone, or an alcohol and a carboxylic acid with the recycling of halide salt. The organic chemical partially oxidized in the process may serve as the source of hydrogen for the reduction of carbon dioxide and acidification of the resulting carboxylic acid. The organic may thereby be indirectly oxidized by carbon dioxide while the carbon dioxide is reduced by the organic such that two or more products are made simultaneously. Advantageously, the halogen employed to partially oxidize an organic and provide hydrogen to the reduction of carbon dioxide or acidification of M-Carboxylate may be recycled.

Figure 1A:
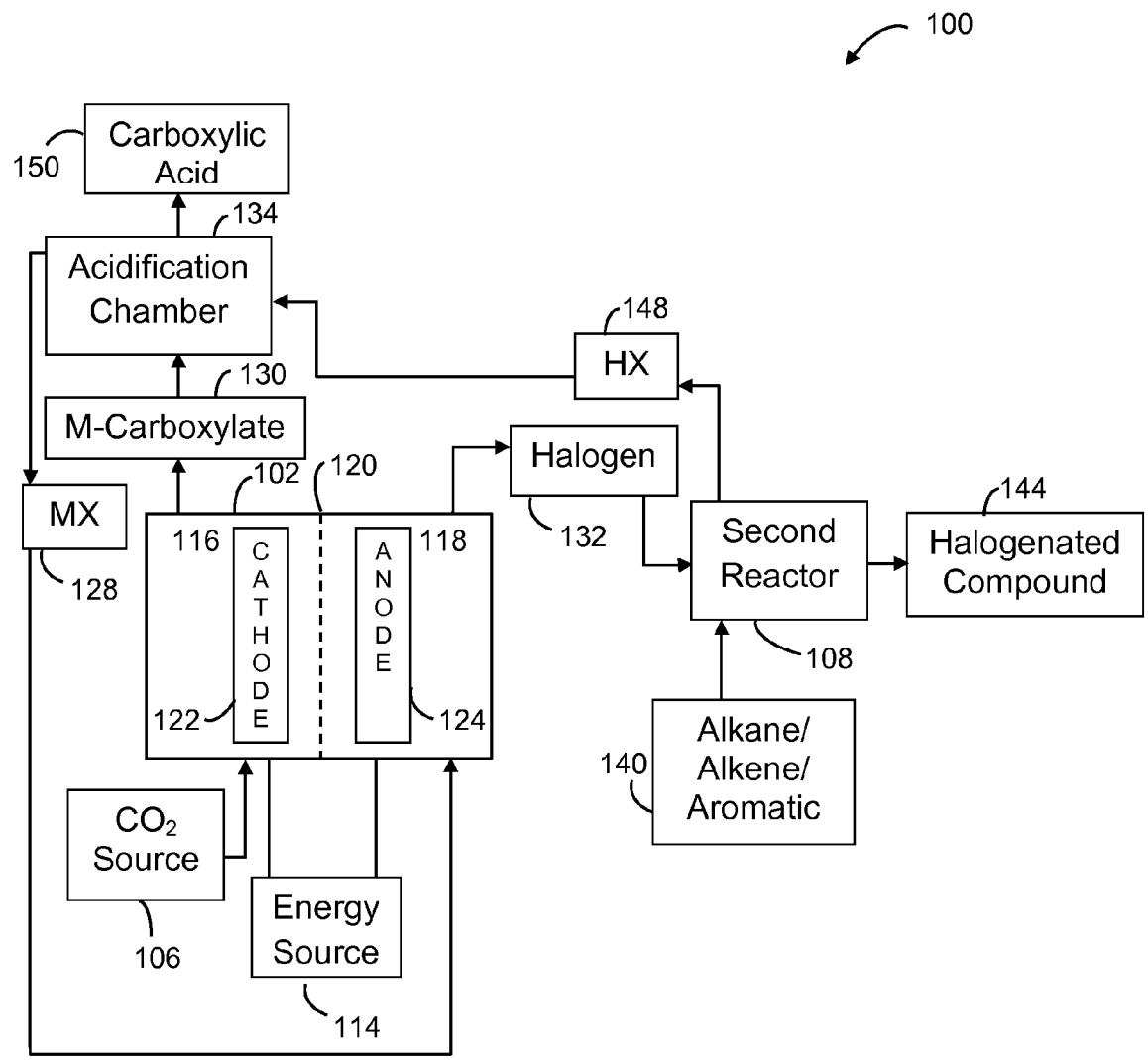
FIG. 1A is a block diagram of a system in accordance with an embodiment of the present disclosure.

Referring to FIG. 1A, a block diagram of a system 100 in accordance with an embodiment of the present disclosure is shown. System (or apparatus) 100 generally includes an electrochemical cell 102. Electrochemical cell 102 may also be referred as a container, electrolyzer, or cell. Electrochemical cell 102 may be implemented as a divided cell. The divided cell may be a divided electrochemical cell and/or a divided photo-electrochemical cell. Electrochemical cell 102 may include a first region 116 and a second region 118. First region 116 and second region 118 may refer to a compartment, section, or generally enclosed space and the like without departing from the scope and intent of the present disclosure. First region 116 may include a cathode 122. Second region 118 may include an anode 124. First region 116 may include a catholyte whereby carbon dioxide from carbon dioxide source 106 is included in the catholyte. Second region 118 may include an anolyte which may include an MX 128 where M is at least one cation and X is selected from a group consisting of F, Cl, Br, I and mixtures thereof. An energy source 114 may generate an electrical potential between the anode 124 and the cathode 122. The electrical potential may be a DC voltage. Energy source 114 may be configured to supply a variable voltage or constant current to electrochemical cell 102. Separator 120 may selectively control a flow of ions between the first region 116 and the second region 118. Separator 120 may include an ion conducting membrane or diaphragm material.

Electrochemical cell 102 is generally operational to reduce carbon dioxide in the first region 116 to an M-carboxylate 130 recoverable from the first region 116, while producing a halogen 132 recoverable from the second region 118.

Carbon dioxide source 106 may provide carbon dioxide to the first region 116 of electrochemical cell 102. In some embodiments, the carbon dioxide is introduced directly into the region 116 containing the cathode 122. It is contemplated that carbon dioxide source 106 may include a source of multiple gases in which carbon dioxide has been filtered from the multiple gases.

It is contemplated that the electrochemical cell 102 may include a first product extractor (not shown) and second product extractor (not shown). Product extractors may implement an organic product and/or inorganic product extractor. The first product extractor (not shown) is generally operational to extract (separate) a product from the first region 116. The second product extractor (not shown) may extract the second product from the second region 118. It is contemplated that the first product extractor and/or second product extractor may be implemented with electrochemical cell 102, or may be remotely located from the electrochemical cell 102. Additionally, it is contemplated that first product extractor and/or second product extractor may be implemented in a variety of mechanisms and to provide desired separation methods, such as fractional distillation, without departing from the scope and intent of the present disclosure. It is further contemplated that extracted product may be presented through a port of the system 100 for subsequent storage and/or consumption by other devices and/or processes.

An anode side of the reaction occurring in the second region 118 of the electrochemical cell 102 may include an input of a recycled reactant of MX 128. The MX 128 may include a halide salt which may be a byproduct of a reaction of acidification chamber 134. For example, the MX 128 may include a halide salt where M is a cation including at least one of Li, Na, K, Cs, Mg, Ca, hydrogen ions, tetraalkyl ammonium ions such as tetrabutylammonium, tetraethylammonium, choline, and tetraalkylphosphonium ions such as tetrabutylphosphonium, tetraethylphosphonium, and in general, $R_1R_2R_3R_4N$ or $R_1R_2R_3R_4P$ where $R_1$ to $R_4$ are independently alkyl, cycloalkyl, branched alkyl, and aryl, and X is selected from a group consisting of F, Cl, Br, I and mixtures thereof. The anode side of the reaction may produce a halogen 132 which may be presented to second reactor 108.

System 100 may include second reactor 108 which may receive halogen 132 produced by the second region 118 of the electrochemical cell 102 after separation from the second region via a second product extractor. Second reactor 108 may react halogen 132 with an alkane, alkene, aromatic, or other compound 140 to produce a halogenated product or halogenated intermediate compound 144 and HX 148. The HX 148 produced in the reaction may be another recycled reactant which may be recycled to the acidification chamber 134 as an input feed to the acidification chamber 134. Examples of halogenated products include monohalogenated, polyhalogenated, and perhalogenated compounds to include chloroform, hydrofluorocarbons, bromoalkanes, vinyl chloride, vinyl bromide, vinyl fluoride, vinylidene fluoride, tetrafluorethane, bromobenzene, dibromobenzene, bromoethane, dichloroethane, allyl chloride, chlorophenol, fluorosurfactants, tetrafluoroethylene, hexafluoropropylene, difluoromethane, or pentafluoroethane.

The acidification chamber 134 of system 100 reacts the HX 148 with the M-carboxylate 130 to produce carboxylic acid 150 and MX 128, which is recycled as an input to the second region 118. The carboxylic acid 150 may be further reacted in an additional reactor with $H_2$ to produce at least one of a more reduced compound. The carboxylic acid 150 may also be reacted with an alcohol to make an ester or diester or be used in other chemical processes. The M-carboxylate 130 may include M-oxalate, M-formate, M-glyoxylate, M-glycolate, or M-acetate in one embodiment.

Figure 1B:
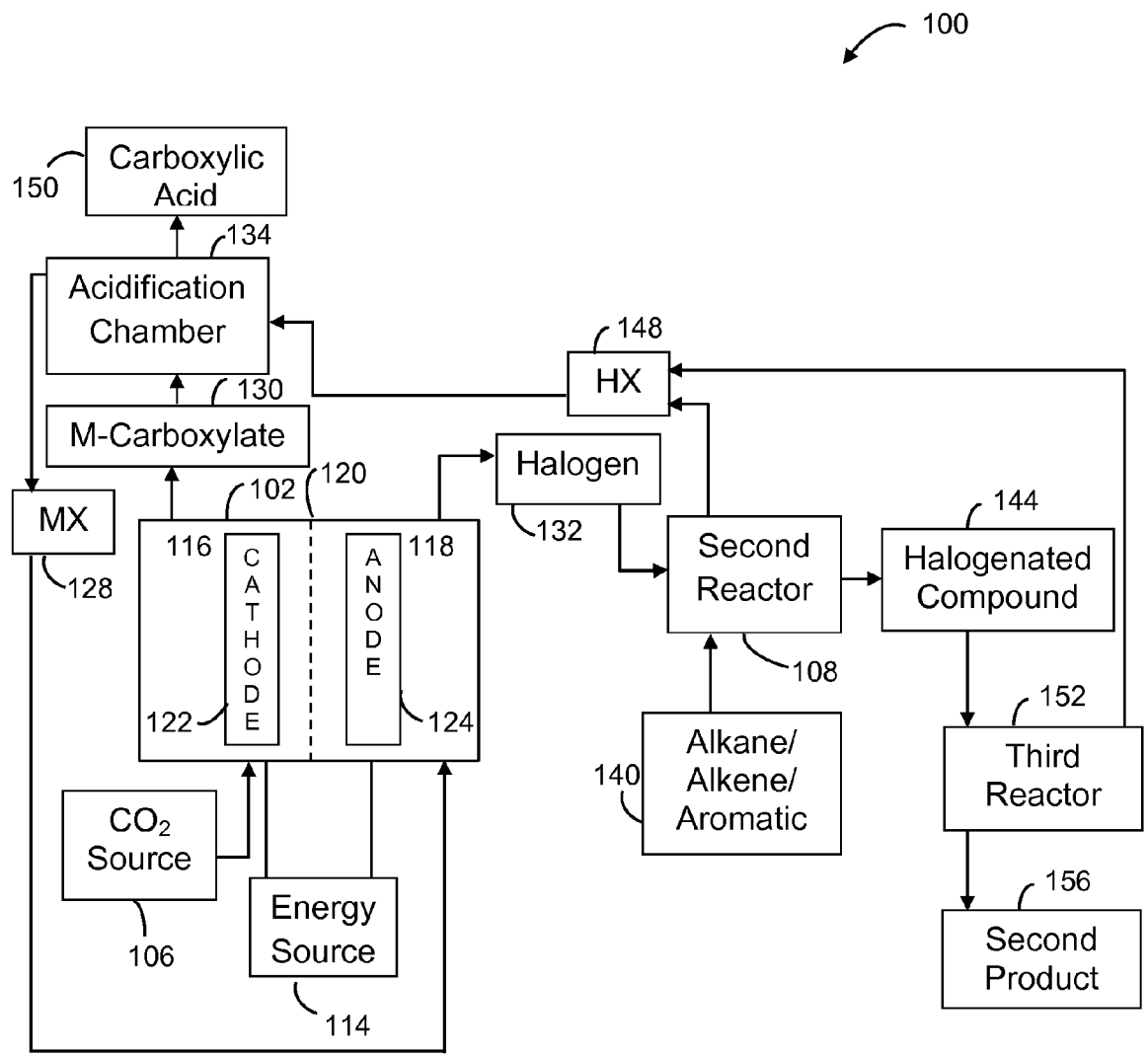
FIG. 1B is a block diagram of a system in accordance with an embodiment of the present disclosure.

In one embodiment shown in FIG. 1B, the system 100 includes an additional reactor, shown as third reactor 152. Halogenated compound 144 may be fed to third reactor 152. In one embodiment, the third reactor 152 is a dehydrohalogenation reactor. Third reactor 152 may perform a dehydrohalogenation reaction of the halogenated compound 144 under specific conditions to produce a second product 156 of an alkene or alkyne. Examples of products derived from the partial oxidation via halogenation and dehalogenation in the second and third reactors are in Table 1 below.

TABLE 1

| Organic Feed | Oxidation Product(s) |
| --- | --- |
| Methane | Methanol, formaldehyde, formic acid, ethylene, longer chain compounds such as ethane |
| Ethane | Ethanol, acetaldehyde, acetic acid, ethylene glycol, ethylene, acetylene, longer chain compounds such as butane |

TABLE 1-continued

| Organic Feed | Oxidation Product(s) |
| --- | --- |
| Ethene (Ethylene) | Acetylene |
| Propane | Propanol, isopropanol, propanone, acetone, propanoic acid, lactic acid, propylene glycol, propylene |
| Butane | Butanol, butane, butadiene |
| Isobutane | Isobutanol, isobutylene |
| Benzene | Phenol |
| Toluene | Benzyl alcohol, benzyl aldehyde, benzoic acid |
| Xylene | Terephthalic acid, isophthalic acid, phthalic acid |
| Ethyl benzene | Styrene |

Figure 2A:
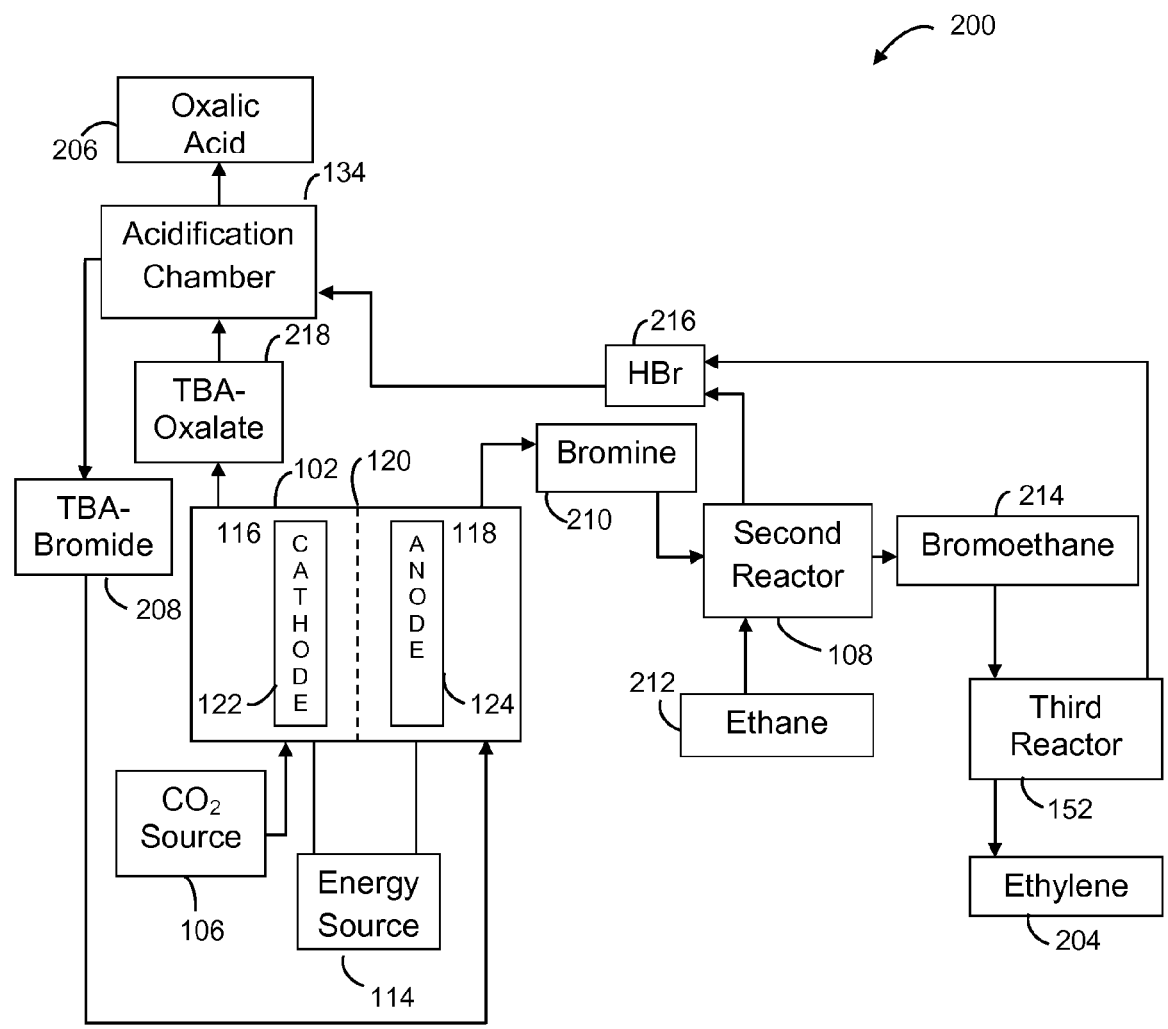
FIG. 2A is a block diagram of a system in accordance with another embodiment of the present disclosure.

An example implementation of the system 100 shown in FIGS. 1A and 1B is shown in FIG. 2A. A system 200 for generating ethylene 204 and oxalic acid 206 from a recycled reactant of tetrabutylammonium bromide (TBA-bromide) 208 and carbon dioxide 106 is provided. Recycled reactant comprised of tetrabutylammonium bromide (TBA-bromide) 208 is fed into the second region 118 of electrochemical cell 102, forming bromine 210. The bromine 210 is extracted from the second region 118 and fed into second reactor 108 where it reacts with ethane 212 to form bromoethane 214 and hydrogen bromide 216. Any byproducts of the halogenation, such as 1,1 dibromoethane or 1,2 dibromoethane, may be separated and sold as a separate product, hydrogenated back to ethane for recycle, or catalytically converted to bromoethane. The hydrogen bromide 216 is recycled to acidification chamber 134. The bromoethane 214 is fed into the third reactor 152, which may be a dehydrohalogenation reactor. The bromoethane 214 is dehydrohalogenated to form ethylene 204.

The cathode 122 side of the reaction of the embodiment shown in FIG. 2A includes the reduction of carbon dioxide in the presence of tetrabutylammonium cations from the reaction in the second region 118, to form tetrabutylammonium oxalate 218. The tetrabutylammonium oxalate 218 is fed into the acidification chamber 134 where it reacts with the recycled hydrogen bromide 216 to produce oxalic acid 206 and tetrabutylammonium bromide 208. The tetrabutylammonium bromide 208 is recycled to the second region 118. The oxalic acid 206 may be further reacted in a thermal hydrogenation chamber with $H_2$ to form a more reduced carbon product, such as glyoxylic acid, glycolic acid, glyoxal, glycolaldeyde, ethlylene glycol, ethanol, acetic acid, actaldehyde, ethane, or ethylene.

Figure 2B:
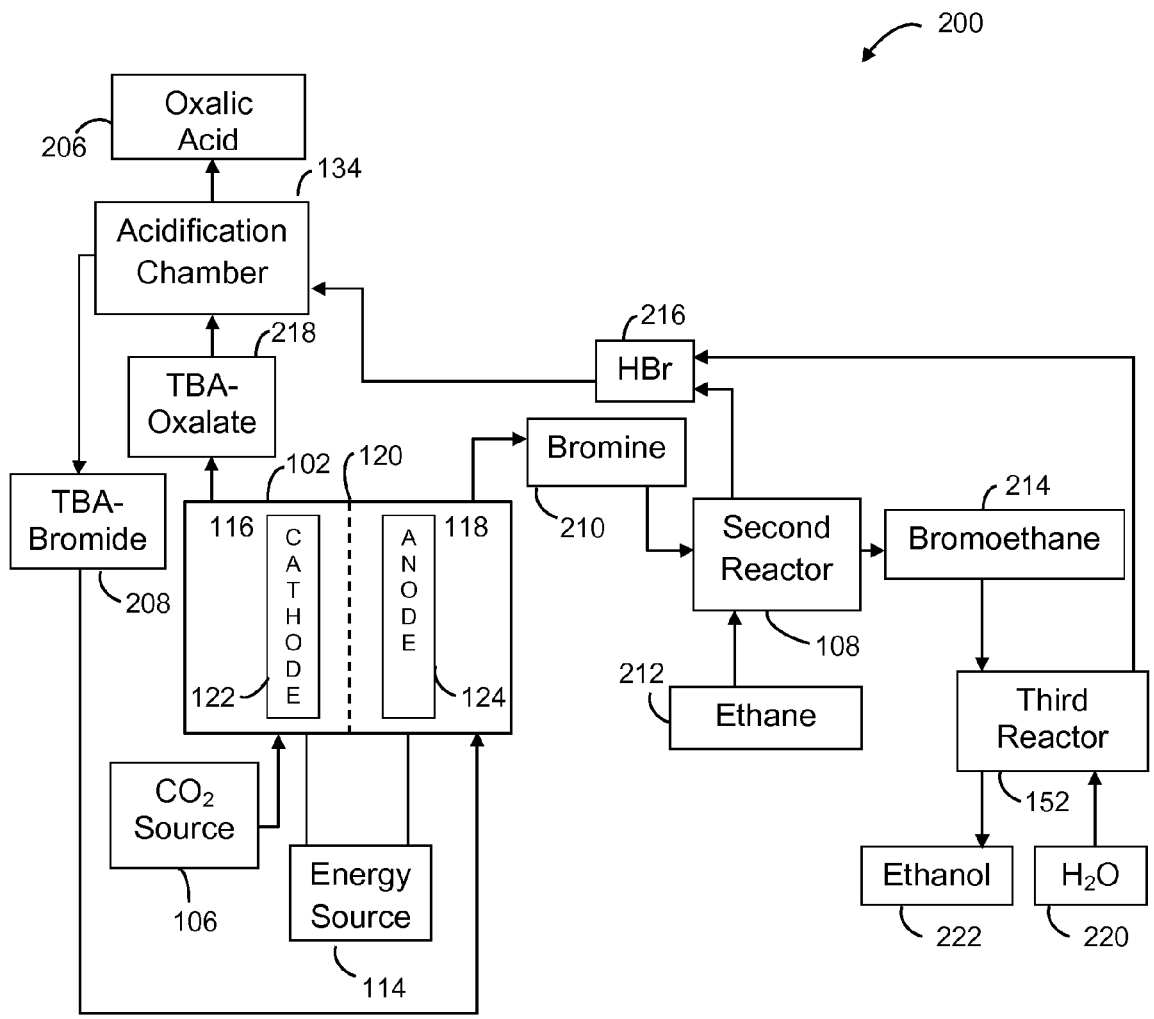
FIG. 2B is a block diagram of a system in accordance with an embodiment of the present disclosure.

In another embodiment shown in FIG. 2B, water 220 may be fed into the third reactor 152 along with the bromoethane 214 to produce ethanol 222 and hydrogen bromide 216.

Figure 3A:
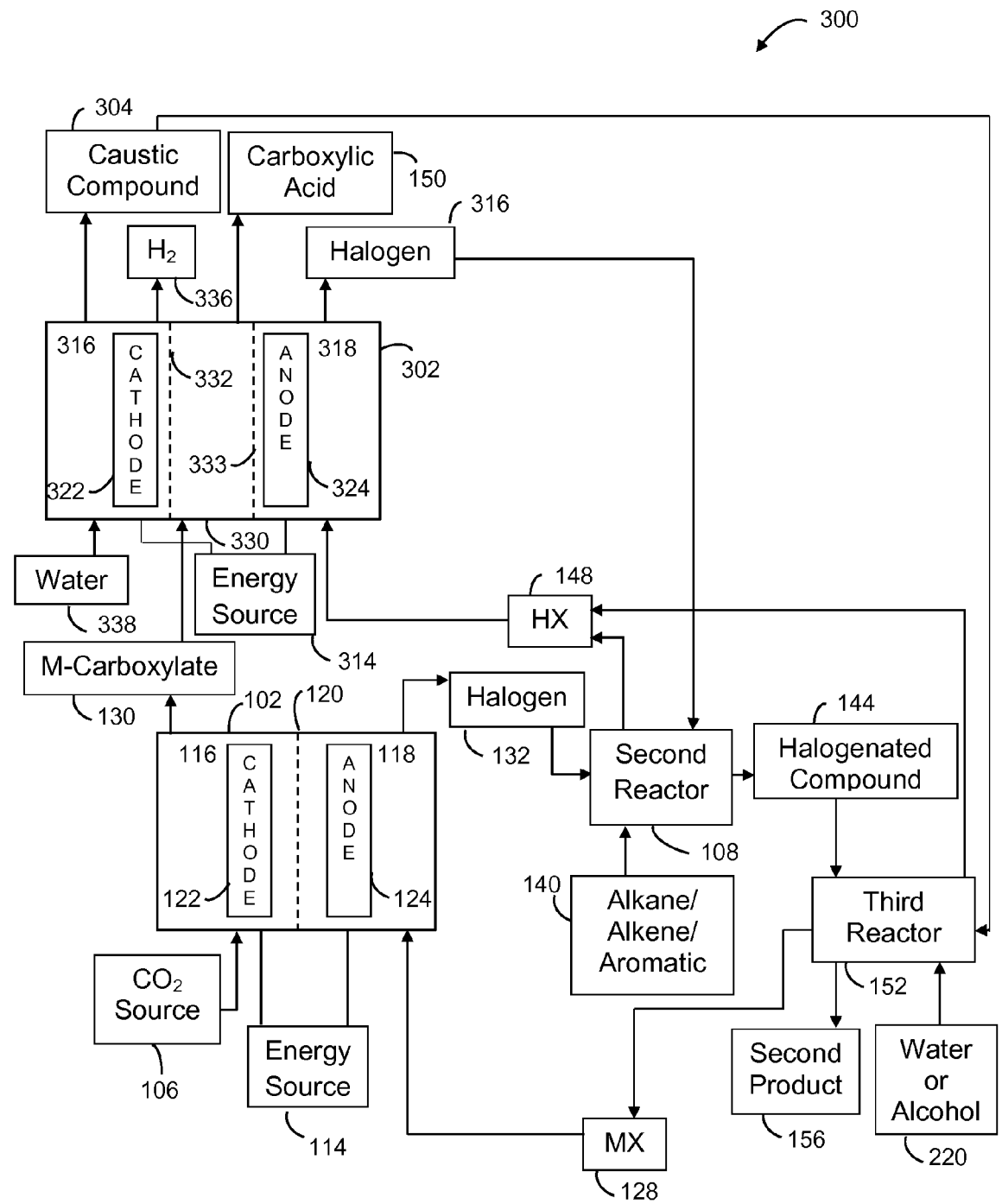
FIG. 3A is a block diagram of a system in accordance with an additional embodiment of the present disclosure.
Figure 3B:
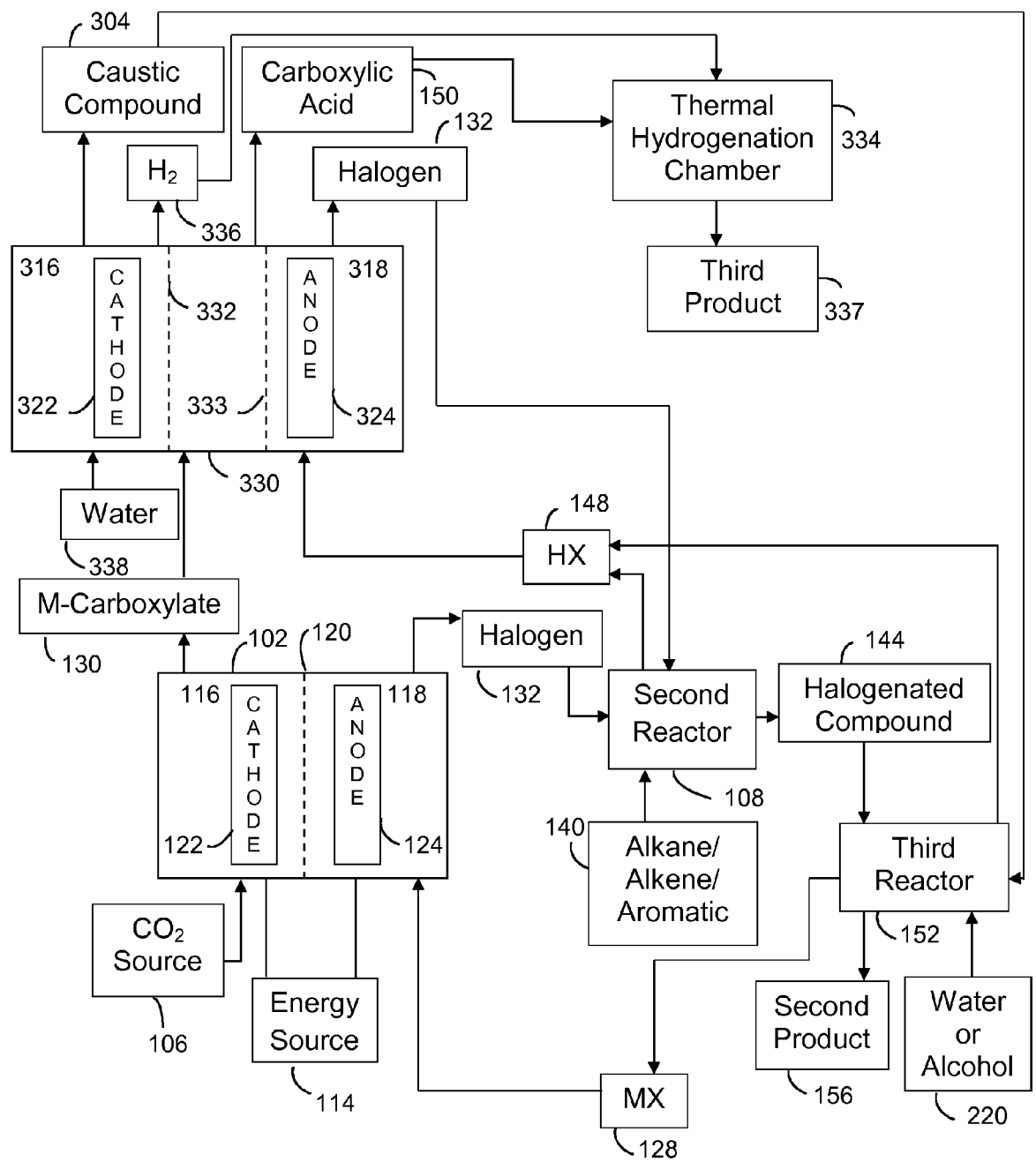
FIG. 3B is a block diagram of a system in accordance with an embodiment of the present disclosure.

A further embodiment of a system in accordance with the present disclosure is provided in FIGS. 3A and 3B which includes electrochemical cell 102, second reactor 108, third reactor 152, and an electrochemical acidification cell 302. The system 300 may be used to form an alkane, alkene, alkyne, aldehyde, ketone, or an alcohol while simultaneously producing a carboxylic acid.

As shown in FIGS. 3A and 3B, electrochemical cell 102 is generally operational to reduce carbon dioxide in the first region 116 to M-carboxylate 130 while oxidizing MX 128 in the second region 118 to produce a halogen 132 recoverable from the second region 118. Specifically, an anode side of the reaction occurring in the second region 118 of the electrochemical cell 102 may include receiving an input of recycled reactant, MX 128. The anode side of the reaction may produce a halogen 132 which may be presented to second reactor 108.

Second reactor 108 may react halogen 132 with an alkane, alkene, aromatic, or other organic compound 140 to produce a halogenated compound 144 and HX 148. HX 148 may be another recycled reactant which may be recycled to the electrochemical acidification cell 302 as an input feed to the electrochemical acidification cell 302. The halogenated compound 144 may be fed to third reactor 152. Third reactor 152 may receive a caustic compound 304 generated from the electrochemical acidification cell 302. The caustic compound 304 may react with the halogenated compound 144 in either an aqueous or non-aqueous based solvent, such as alcohol, 220 to produce a second product 156 as well as MX 128. If the reaction occurs in the presence of an aqueous solvent, the second product 156 may be an alcohol. If the reaction occurs in the presence of a non-aqueous alcohol based solvent, the second product 156 may be an alkene or alkyne. The MX 128 produced in the third reactor 152 may be recycled to the second region 118 of the electrochemical cell 102.

The caustic compound 304 may include MOH in one embodiment, where M represents the cation used in the reaction. An example of MOH may include NaOH or KOH in one embodiment. The caustic compound 304 may include a caustic metallic base in one embodiment.

Meanwhile, carbon dioxide source 106 may provide carbon dioxide to the first region 116 of electrochemical cell 102. In some embodiments, the carbon dioxide is introduced directly into the region 116 containing the cathode 122. Carbon dioxide is reduced in the first region 116 and reacts with the ions from the anode reaction to produce M-carboxylate 130. The M-carboxylate 130 may be extracted from the first region 116 and fed into an electrochemical acidification cell 302.

Electrochemical acidification cell 302 may include a first region 316 and a second region 318. First region 316 and second region 318 may refer to a compartment, section, or generally enclosed space, and the like without departing from the scope and intent of the present disclosure. First region 316 may include a cathode 322. Second region 318 may include an anode 324. First region 316 may include a catholyte comprising water. Second region 318 may include an anolyte which may include HX 148, which is provided from the second reactor 108 and/or the third reactor 152 and recycled to the anolyte. An energy source 314 may generate an electrical potential between the anode 324 and the cathode 322. Electrochemical acidification cell may also include an acidification region 330. A first separator 332 and a second separator 333 may selectively control a flow of ions between the first region 316, acidification region 330, and the second region 318. The first separator 332 and the second separator 333 may include an ion conducting membrane or diaphragm material.

The electrochemical acidification cell 302 may receive three different inputs. First, M-carboxylate 130 produced by the first region 116 of the electrochemical cell 102 may be fed into the acidification region 330 of the electrochemical acidification cell 302 where it is acidified to form the first product, carboxylic acid, 150, liberating M cations which are transported to the first region 316. Second, HX 148 may be recycled from the second reactor 108 to the second region 318 of electrochemical acidification cell 302 to form more of the halogen, liberating W cations, or protons, for transport into the acidification region 330. The protons displace or replace the M cations of the M-carboxalate in the acidification region 330, which then pass through membrane 332 into region 316 of the catholyte. The halogen 316 produced in the second region 318 of the electrochemical acidification cell 302 is then removed from the second region 318 and recycled as an input to the second reactor 108. A third input to the electrochemical acidification cell 302 may include a water source 338 which is fed to the first region 316. The water 338 is reduced to $H_2$ and $OH^-$ at cathode 322, and the OH— reacts with the M cations passing from the acidification region through membrane 332 to form the caustic compound 304. The caustic compound 304 is then removed from the first region 316 and may be recycled as an input to the third reactor 152. $H_2$ 336 may also be produced in the first region.

In one embodiment shown in FIG. 3B, the system 300 may include an additional reactor including a thermal hydrogenation chamber 334. The thermal hydrogenation chamber 334 may react the $H_2$ 336 produced in the first region of the electrochemical acidification cell 302 as well as the first product, carboxylic acid 150 produced in the acidification region 330 of the electrochemical acidification cell 302 to produce a third product 337. The third product may include glyoxylic acid, glycolic acid, glyoxal, glycolaldehyde, acetic acid, acetaldehyde, ethanol, ethane, ethylene, or ethylene glycol.

Figure 4:
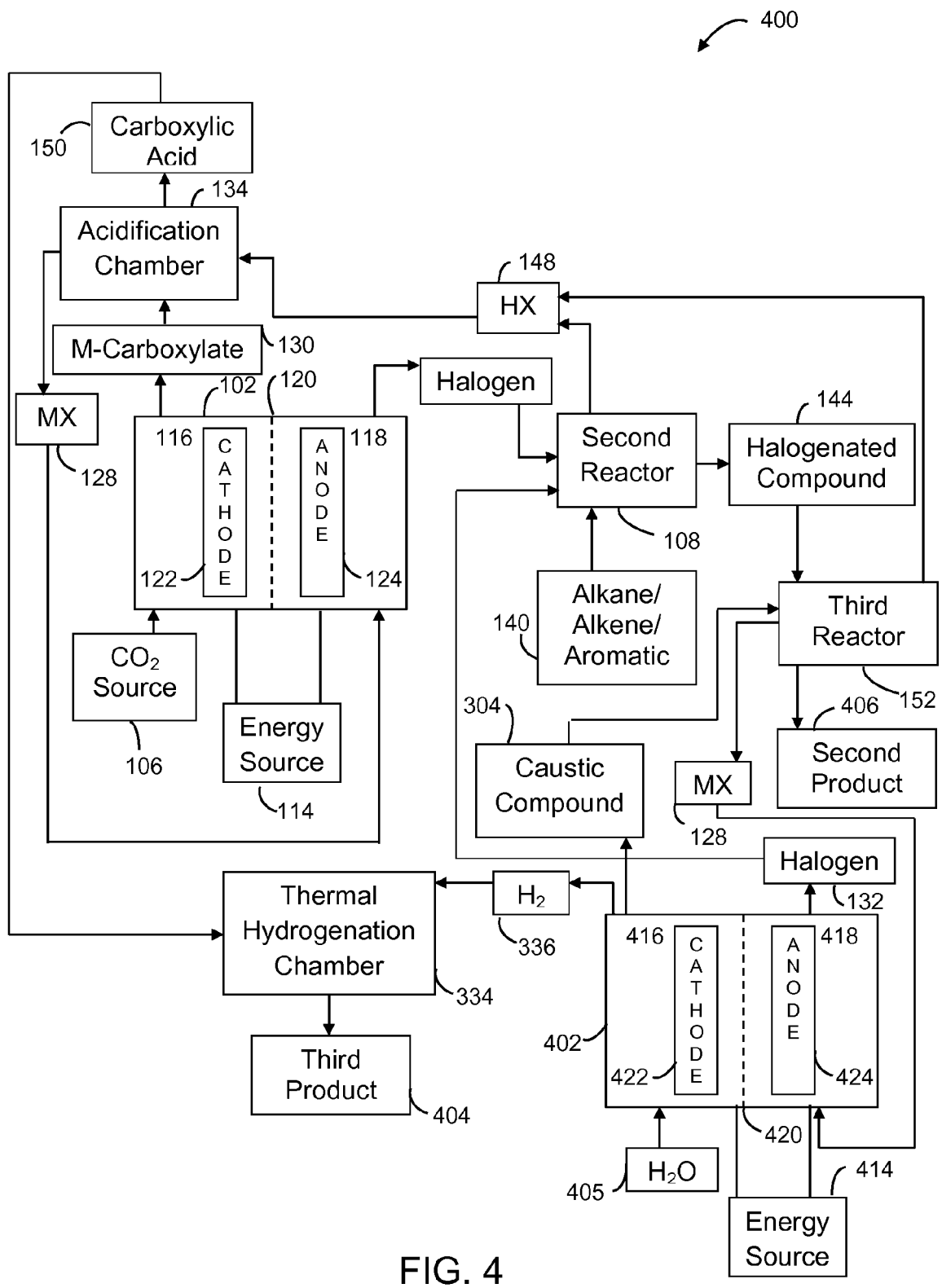
FIG. 4 is a block diagram of a system in accordance with another additional embodiment of the present disclosure.

A further embodiment of a system in accordance with the present disclosure is provided in FIG. 4 which includes a first electrochemical cell 102, second reactor 108, third reactor 152, a second electrochemical cell 402, and a thermal hydrogenation chamber 334. The system 400 may be used to form an alkene, alkyne, aldehyde, ketone, or an alcohol (second product 406) while simultaneously producing at least one of glyoxylic acid, glycolic acid, glyoxal, glycolaldehyde, acetic acid, acetaldehyde, ethanol, ethane, ethylene, or ethylene glycol (third product 404).

As shown in FIG. 4, first electrochemical cell 102 is generally operational to reduce carbon dioxide in the first region 116 to M-carboxylate 130 recoverable from the first region 116, while oxidizing MX 128 in the second region 118 to produce a halogen 132 recoverable from the second region 118. The halogen 132 may be extracted from the second region 118 and input to a second reactor.

The second reactor 108 may react the halogen 132 with an alkane, alkene, aromatic, or other aromatic compound 140 to produce a halogenated compound 144 and HX 148. HX 148 may then be recycled to an acidification chamber 134 as an input feed to the acidification chamber 134. The halogenated compound 144 may be fed to third reactor 152. Third reactor 152 may receive a caustic compound 304 recycled from the second two compartment electrochemical cell 402. The caustic compound 304 reacts with the halogenated compound 144 in the third reactor to produce a second product 406 as well as MX 128. The MX 128 may be recycled as an input feed to a second region 418 of the second electrochemical cell 402.

If the reaction of the halogenated compound 144 and the caustic compound 304 in the third reactor 152 occurs in the presence of water, the second product 406 may be an alcohol. If the reaction occurs in the presence of a non-aqueous solvent, such as an alcohol, the second product 406 may be an alkene or alkyne. In one embodiment, the second product 406 is ethanol. In another embodiment, the second product 406 is ethylene. In another embodiment, the second product is phenol derived from benzene. In yet another embodiment, the second product is isopropanol derived from propane or propylene.

The MX 128 produced in the third reactor 152 may be recycled as an input feed to a second region 418 of the second electrochemical cell 402. The second electrochemical cell 402 may include a first region 416 and a second region 418. First region 416 may include a cathode 422. Second region 418 may include an anode 424. First region 416 may include a catholyte comprising water. Second region 318 may include an anolyte which may include MX 128, which is provided from the third reactor 152 and recycled to the anolyte. An energy source 414 may generate an electrical potential between the anode 424 and the cathode 422. A separator 420 may control the flow of ions between the first region 416 and the second region 418.

The second electrochemical cell 402 may receive an input of the MX 128 produced in the third reactor 152 as an input feed to the second region 418 of the second electrochemical cell 402 where it is oxidized to produce halogen 132, liberating M cations to be transported through separator 420 to the first region 416. Halogen 132 is then removed from the second region 418 and recycled as an input to the second reactor 108. An additional input to the second electrochemical cell 402 may include water 405 which is fed to the first region 416. The water 405 is reduced to $H_2$ and OH— at cathode 422. The OH— hydroxide ions react with M cations provided by the reaction at the second region 418 to form the caustic compound 304. The caustic compound 304 is then removed from the first region 416 and may be recycled as an input to the third reactor 152. $H_2$ 336 may also be produced in the first region, which may be recycled as an input feed to thermal hydrogenation chamber 334. Hydrogen for the thermal hydrogenation chamber 334 may be supplied from other sources as well.

The cathode side of the reaction in the first electrochemical cell 102 consists of the reduction of carbon dioxide provided by carbon dioxide source 106 along with ions from the reaction on the anode side to form M-carboxylate 130. The M-carboxylate 130 may be removed from the first region 116 and input into acidification chamber 134. The acidification chamber 134 reacts the HX 148 provided by the second reactor 108 with the M-carboxylate 130 to produce the carboxylic acid 150 (first product) and MX 128. The MX 128 is recycled as an input to the second region. The carboxylic acid 150 is then fed to thermal hydrogenation chamber 334.

The first product, carboxylic acid 150 from the acidification chamber 134 is then fed to thermal hydrogenation chamber 334 where it reacts with $H_2$ 336 provided by the first region 416 of the second electrochemical cell 402 to produce the third product 404. Additional $H_2$ may be provided from another source.

It is contemplated that a receiving feed may include various mechanisms for receiving a supply of a product, whether in a continuous, near continuous or batch portions.

It is further contemplated that the structure and operation of the electrochemical cells 102 and 402 as well as the electrochemical acidification cell 302 and may be adjusted to provide desired results. For example, the electrochemical cells may operate at higher pressures, such as pressure above atmospheric pressure which may increase current efficiency and allow operation of the electrochemical cell at higher current densities.

Additionally, the cathode 122 and anode 124 may include a high surface area electrode structures with a void volume which may range from 30% to 98%. The electrode void volume percentage may refer to the percentage of empty space that the electrode is not occupying in the total volume space of the electrode. The advantage in using a high void volume electrode is that the structure has a lower pressure drop for liquid flow through the structure. The specific surface area of the electrode base structure may be from 2 $cm^2/cm^3$ to 500 $cm^2/cm^3$ or higher. The electrode specific surface area is a ratio of the base electrode structure surface area divided by the total physical volume of the entire electrode. It is contemplated that surface areas also may be defined as a total area of the electrode base substrate in comparison to the projected geometric area of the current distributor/conductor back plate, with a preferred range of 2× to 1000× or more. The actual total active surface area of the electrode structure is a function of the properties of the electrode catalyst deposited on the physical electrode structure which may be 2 to 1000 times higher in surface area than the physical electrode base structure.

Cathode 122 may be selected from a number of high surface area materials to include copper, stainless steels, transition metals and their alloys and oxides, carbon, and silicon, which may be further coated with a layer of material which may be a conductive metal or semiconductor. The base structure of cathode 122 may be in the form of fibrous, reticulated, or sintered powder materials made from metals, carbon, or other conductive materials including polymers. The materials may be a very thin plastic screen incorporated against the cathode side of the membrane to prevent the membrane 120 from directly touching the high surface area cathode structure. The high surface area cathode structure may be mechanically pressed against a cathode current distributor backplate, which may be composed of material that has the same surface composition as the high surface area cathode.

In addition, cathode 122 may be a suitable conductive electrode, such as Al, Au, Ag, Bi, C, Cd, Co, Cr, Cu, Cu alloys (e.g., brass and bronze), Ga, Hg, In, Mo, Nb, Ni, $NiCo_2O_4$, Ni alloys (e.g., Ni 625, NiHX), Ni—Fe alloys, Pb, Pd alloys (e.g., PdAg), Pt, Pt alloys (e.g., PtRh), Rh, Sn, Sn alloys (e.g., SnAg, SnPb, SnSb), Ti, V, W, Zn, stainless steel (SS) (e.g., SS 2205, SS 304, SS 316, SS 321), austenitic steel, ferritic steel, duplex steel, martensitic steel, Nichrome (e.g., NiCr 60:16 (with Fe)), elgiloy (e.g., Co—Ni—Cr), degenerately doped p-Si, degenerately doped p-Si:As, degenerately doped p-Si:B, degenerately doped n-Si, degenerately doped n-Si:As, and degenerately doped n-Si:B. These metals and their alloys may also be used as catalytic coatings on the various metal substrates. Other conductive electrodes may be implemented to meet the criteria of a particular application. For photo-electrochemical reductions, cathode 122 may be a p-type semiconductor electrode, such as p-GaAs, p-GaP, p-InN, p-InP, p-CdTe, p-GaInP$_2$ and p-Si, or an n-type semiconductor, such as n-GaAs, n-GaP, n-InN, n-InP, n-CdTe, n-GaInP$_2$ and n-Si. Other semiconductor electrodes may be implemented to meet the criteria of a particular application including, but not limited to, CoS, $MoS_2$, TiB, $WS_2$, SnS, $Ag_2S$, $CoP_2$, $Fe_3P$, $Mn_3P_2$, MoP, $Ni_2Si$, $MoSi_2$, WSi2, $CoSi_2$, $Ti_4O_7$, $SnO_2$, GaAs, GaSb, Ge, and CdSe.

Catholyte may include a pH range from 1 to 12 when aqueous solvents are employed, preferably from pH 4 to pH 10. The selected operating pH may be a function of any catalysts utilized in operation of the electrochemical cell 102. Preferably, catholyte and catalysts may be selected to prevent corrosion at the electrochemical cell 102. Catholyte may include homogeneous catalysts. Homogeneous catalysts are defined as aromatic heterocyclic amines and may include, but are not limited to, unsubstituted and substituted pyridines and imidazoles. Substituted pyridines and imidazoles may include, but are not limited to mono and disubstituted pyridines and imidazoles. For example, suitable catalysts may include straight chain or branched chain lower alkyl (e.g., $C_1$-$C_{10}$) mono and disubstituted compounds such as 2-methylpyridine, 4-tertbutyl pyridine, 2,6 dimethylpyridine (2,6-lutidine); bipyridines, such as 4,4'-bipyridine; amino-substituted pyridines, such as 4-dimethylamino pyridine; and hydroxyl-substituted pyridines (e.g., 4-hydroxy-pyridine) and substituted or unsubstituted quinoline or isoquinolines. The catalysts may also suitably include substituted or unsubstituted dinitrogen heterocyclic amines, such as pyrazine, pyridazine and pyrimidine. Other catalysts generally include azoles, imidazoles, indoles, oxazoles, thiazoles, substituted species and complex multi-ring amines such as adenine, pterin, pteridine, benzimidazole, phenonthroline and the like.

The catholyte may include an electrolyte. Catholyte electrolytes may include alkali metal bicarbonates, carbonates, sulfates, phosphates, borates, and hydroxides. The electrolyte may comprise one or more of $Na_2SO_4$, KCl, $NaNO_3$, NaCl, NaF, $NaClO_4$, $KClO_4$, $K_2SiO_3$, $CaCl_2$, a guanidinium cation, an H cation, an alkali metal cation, an ammonium cation, an alkylammonium cation, a tetraalkyl ammonium cation, a halide anion, an alkyl amine, a borate, a carbonate, a guanidinium derivative, a nitrite, a nitrate, a phosphate, a polyphosphate, a perchlorate, a silicate, a sulfate, and a hydroxide. In one embodiment, bromide salts such as NaBr or KBr may be preferred.

The catholyte may further include an aqueous or non-aqueous solvent. An aqueous solvent may include greater than 5% water. A non-aqueous solvent may include as much as 5% water. A solvent may contain one or more of water, a protic solvent, or an aprotic polar solvent. Representative solvents include methanol, ethanol, acetonitrile, propylene carbonate, ethylene carbonate, dimethyl carbonate, diethyl carbonate, dimethylsulfoxide, dimethylformamide, acetonitrile, acetone, tetrahydrofuran, N,N-dimethylacetaminde, dimethoxyethane, diethylene glycol dimethyl ester, butyrolnitrile, 1,2-difluorobenzene, γ-butyrolactone, N-methyl-2-pyrrolidone, sulfolane, 1,4-dioxane, nitrobenzene, nitromethane, acetic anhydride, ionic liquids, and mixtures thereof.

In one embodiment, a catholyte/anolyte flow rate may include a catholyte/anolyte cross sectional area flow rate range such as 2-3,000 gpm/ft$^2$ or more (0.0076-11.36 m$^3$/m$^2$). A flow velocity range may be 0.002 to 20 ft/sec (0.0006 to 6.1 m/sec). Operation of the electrochemical cell catholyte at a higher operating pressure allows more dissolved carbon dioxide to dissolve in the aqueous solution. Typically, electrochemical cells can operate at pressures up to about 20 to 30 psig in multi-cell stack designs, although with modifications, the electrochemical cells may operate at up to 100 psig. The electrochemical cell may operate anolyte at the same pressure range to minimize the pressure differential on a separator 120 or membrane separating the two regions. Special electrochemical designs may be employed to operate electrochemical units at higher operating pressures up to about 60 to 100 atmospheres or greater, which is in the liquid $CO_2$ and supercritical $CO_2$ operating range.

In another embodiment, a portion of a catholyte recycle stream may be separately pressurized using a flow restriction with back pressure or using a pump, with $CO_2$ injection, such that the pressurized stream is then injected into the catholyte region of the electrochemical cell which may increase the amount of dissolved $CO_2$ in the aqueous solution to improve the conversion yield. In addition, micro-bubble generation of carbon dioxide can be conducted by various means in the catholyte recycle stream to maximize carbon dioxide solubility in the solution.

Catholyte may be operated at a temperature range of −10 to 95° C., more preferably 5-60° C. The lower temperature will be limited by the catholytes used and their freezing points. In general, the lower the temperature, the higher the solubility of $CO_2$ in an aqueous solution phase of the catholyte, which would help in obtaining higher conversion and current efficiencies. The drawback is that the operating electrochemical cell voltages may be higher, so there is an optimization that would be done to produce the chemicals at the lowest operating cost. In addition, the catholyte may require cooling, so an external heat exchanger may be employed, flowing a portion, or all, of the catholyte through the heat exchanger and using cooling water to remove the heat and control the catholyte temperature.

Anolyte operating temperatures may be in the same ranges as the ranges for the catholyte, and may be in a range of 0° C. to 95° C. In addition, the anolyte may require cooling, so an external heat exchanger may be employed, flowing a portion, or all, of the anolyte through the heat exchanger and using cooling water to remove the heat and control the anolyte temperature.

Electrochemical cells may include various types of designs. These designs may include zero gap designs with a finite or zero gap between the electrodes and membrane, flow-by and flow-through designs with a recirculating catholyte electrolyte utilizing various high surface area cathode materials. The electrochemical cell may include flooded co-current and counter-current packed and trickle bed designs with the various high surface area cathode materials. Also, bipolar stack cell designs and high pressure cell designs may also be employed for the electrochemical cells.

Anode electrodes may be the same as cathode electrodes or different. Anodes 124, 324, and 424 may include electrocatalytic coatings applied to the surfaces of the base anode structure. Anolytes may be the same as catholytes or different. Anolyte electrolytes may be the same as catholyte electrolytes or different. Anolyte may comprise solvent. Anolyte solvent may be the same as catholyte solvent or different. For example, for HBr, acid anolytes, and oxidizing water generating oxygen, the preferred electrocatalytic coatings may include precious metal oxides such as ruthenium and iridium oxides, as well as platinum and gold and their combinations as metals and oxides on valve metal substrates such as titanium, tantalum, zirconium, or niobium. For bromine and iodine anode chemistry, carbon and graphite are particularly suitable for use as anodes. Polymeric bonded carbon material may also be used. For other anolytes, comprising alkaline or hydroxide electrolytes, anodes may include carbon, cobalt oxides, stainless steels, transition metals, and their alloys and combinations. High surface area anode structures that may be used which would help promote the reactions at the anode surfaces. The high surface area anode base material may be in a reticulated form composed of fibers, sintered powder, sintered screens, and the like, and may be sintered, welded, or mechanically connected to a current distributor back plate that is commonly used in bipolar electrochemical cell assemblies. In addition, the high surface area reticulated anode structure may also contain areas where additional applied catalysts on and near the electrocatalytic active surfaces of the anode surface structure to enhance and promote reactions that may occur in the bulk solution away from the anode surface such as the reaction between bromine and the carbon based reactant being introduced into the anolyte. The anode structure may be gradated, so that the density of the may vary in the vertical or horizontal direction to allow the easier escape of gases from the anode structure. In this gradation, there may be a distribution of particles of materials mixed in the anode structure that may contain catalysts, such as metal halide or metal oxide catalysts such as iron halides, zinc halides, aluminum halides, cobalt halides, for the reactions between the bromine and the carbon-based reactant. For other anolytes comprising alkaline, or hydroxide electrolytes, anodes may include carbon, cobalt oxides, stainless steels, and their alloys and combinations.

Separator also referred to as a membrane, between a first region and second region, may include cation ion exchange type membranes. Cation ion exchange membranes which have high rejection efficiency to anions may be preferred. Examples of such cation ion exchange membranes may include perfluorinated sulfonic acid based ion exchange membranes such as DuPont Nafion® brand unreinforced types N117 and N120 series, more preferred PTFE fiber reinforced N324 and N424 types, and similar related membranes manufactured by Japanese companies under the supplier trade names such as AGC Engineering (Asahi Glass) under their trade name Flemion®. Other multi-layer perfluorinated ion exchange membranes used in the chlor alkali industry may have a bilayer construction of a sulfonic acid based membrane layer bonded to a carboxylic acid based membrane layer, which efficiently operates with an anolyte and catholyte above a pH of about 2 or higher. These membranes may have higher anion rejection efficiency. These are sold by DuPont under their Nafion® trademark as the N900 series, such as the N90209, N966, N982, and the 2000 series, such as the N2010, N2020, and N2030 and all of their types and subtypes. Hydrocarbon based membranes, which are made from of various cation ion exchange materials can also be used if the anion rejection is not as desirable, such as those sold by Sybron under their trade name Ionac®, AGC Engineering (Asahi Glass) under their Selemion® trade name, and Tokuyama Soda, among others on the market. Ceramic based membranes may also be employed, including those that are called under the general name of NASICON (for sodium super-ionic conductors) which are chemically stable over a wide pH range for various chemicals and selectively transports sodium ions, the composition is $Na_1+xZr_2Si_xP_3-xO_{12}$, and well as other ceramic based conductive membranes based on titanium oxides, zirconium oxides and yttrium oxides, and beta aluminum oxides. Alternative membranes that may be used are those with different structural backbones such as polyphosphazene and sulfonated polyphosphazene membranes in addition to crown ether based membranes. Preferably, the membrane or separator is chemically resistant to the anolyte and catholyte and operates at temperatures of less than 600 degrees C., and more preferably less than 500 degrees C.

A rate of the generation of reactant formed in the anolyte compartment from the anode reaction is contemplated to be proportional to the applied current to the electrochemical cell. The anolyte product output in this range can be such that the output stream contains little or no free bromine in the product output, or it may contain unreacted bromine. The operation of the extractor and its selected separation method, for example fractional distillation, the actual products produced, and the selectivity may be adjusted to obtain desired characteristics. Any of the unreacted components would be recycled to the second region.

Similarly, a rate of the generation of the formed electrochemical carbon dioxide reduction product, such as CO, is contemplated to be proportional to the applied current to the electrochemical cell. The rate of the input or feed of the carbon dioxide source 106 should be fed in a proportion to the applied current. The cathode reaction efficiency would determine the maximum theoretical formation in moles of the carbon dioxide reduction product. It is contemplated that the ratio of carbon dioxide feed to the theoretical moles of potentially formed carbon dioxide reduction product would be in a range of 100:1 to 2:1, and preferably in the range of 50:1 to 5:1, where the carbon dioxide is in excess of the theoretical required for the cathode reaction. The carbon dioxide excess would then be separated and recycled back to the first region 116.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A method for co-producing M-carboxylate and a halogen, the method comprising the steps of:
   contacting a first region of an electrochemical cell having a cathode with a catholyte comprising carbon dioxide;
   contacting a second region of the electrochemical cell having an anode with an anolyte comprising an MX where M is at least one cation and X is selected from the group consisting of F, Cl, Br, I and mixtures thereof;
   applying an electrical potential between the anode and the cathode of the electrochemical cell sufficient to produce the M-carboxylate recoverable from the first region of the electrochemical cell and the halogen recoverable from the second region of the electrochemical cell;
   reacting the halogen from the second region of the electrochemical cell with one of an alkane, an alkene, or an aromatic to produce a halogenated compound and HX, the HX being recycled back to an acidification chamber;
   reacting the M-carboxylate with the HX via the acidification chamber to produce a carboxylic acid and MX, the MX being recycled to an input of the second region of the electrochemical cell.

2. The method according to claim 1, further comprising:
   reacting the halogenated compound via a third reactor to produce the second product and HX, the HX being recycled to the acidification chamber.

3. The method according to claim 1, wherein the halogen includes at least one of $F_2$, $Cl_2$, $Br_2$ or $I_2$.

4. The method according to claim 1, wherein the halogenated compound includes at least one of a brominated compound, benzyl bromide, (1-bromethyl) benzene, perhalo carbon, bromoethane, vinyl chloride, dichloroethane, allyl chloride, chlorophenol, bromobenzene, vinyl bromide, vinyl fluoride, vinylidene fluoride, tetrafluoroethylene, hexafluoropropylene, difluoromethane, or pentafluoroethane.

5. The method according to claim 2, wherein the second product is at least one of an alkane, an alkene, an alkyne, an alcohol, an aldehyde, or a ketone.

6. The method according to claim 2, wherein the third reactor includes water.

7. The method according to claim 1, wherein the carboxylic acid is oxalic acid.

8. The method according to claim 1, further comprising:
   feeding the carboxylic acid to a thermal hydrogenation chamber, the thermal hydrogenation chamber comprising $H_2$; and
   forming a third product in the thermal hydrogenation chamber.

9. The method according to claim 8, wherein the third product includes at least one of glyoxylic acid, glycolic acid, glyoxal, glycolaldeyde, ethylene glycol, ethanol, acetic acid, acetaldehyde, ethane, or ethylene.

10. The method according to claim 1, wherein the cathode and the anode of the first electrochemical cell and the second electrochemical cell are separated by an ion permeable barrier that operates at a temperature less than 600 degrees C.

11. The method according to claim 1, wherein the ion permeable barrier includes one of a polymeric or inorganic ceramic-based ion permeable barrier.

12. The method according to claim 1, wherein the catholyte is a liquid and the anolyte is a gas.

13. The method according to claim 1, further comprising:
   reacting the carboxylic acid with $H_2$ to form a third product via a thermal hydrogenation chamber;
   reacting the halogenated compound with a caustic compound via a third reactor to produce the second product and MX, the MX being recycled to an input of a second region of a second electrochemical cell, the second electrochemical cell comprising a first region having a cathode and the second region having an anode;
   contacting the first region of the second electrochemical cell with a catholyte comprising water;
   contacting the second region of the second electrochemical cell with the MX from the third reactor;
   applying an electrical potential between the anode and the cathode of the second electrochemical cell sufficient to produce $H_2$ and the caustic compound recoverable from the first region of the second electrochemical cell and a halogen recoverable from the second region of the second electrochemical cell;
   feeding the $H_2$ from the second electrochemical cell to the thermal hydrogenation chamber;
   feeding the caustic compound from the second electrochemical cell to the third reactor;
   feeding the halogen recoverable from the second region of the second electrochemical cell to the second reactor.

14. The method according to claim 13 wherein the second product is at least one of an alcohol, an alkene, an alkyne, an aldehyde, a ketone, an alkane, and mixtures thereof.

15. The method according to claim 8, wherein the third product includes at least one of glyoxylic acid, glycolic acid, glyoxal, glycolaldeyde, ethylene glycol, ethanol, acetic acid, acetaldehyde, ethane, or ethylene.

16. A method for co-producing M-carboxylate and a halogen, the method comprising the steps of:
   contacting a first region of a first electrochemical cell having an cathode with a catholyte comprising carbon dioxide;
   contacting a second region of a first electrochemical cell having an anode with an anolyte comprising an MX where M is at least one cation and X is selected from the group consisting of F, Cl, Br, I, and mixtures thereof;
   applying an electrical potential between the anode and the cathode of the electrochemical cell sufficient to co-produce the M-carboxylate recoverable from the first region of the first electrochemical cell and the halogen recoverable from the second region of the first electrochemical cell;
   reacting the halogen with at least one of an alkane, alkene, or aromatic to form a halogenated compound and HX via a secondary reactor, the HX being recycled to an input of a second region of an electrochemical acidification cell;
   reacting the halogenated compound with a caustic compound to form MX and the second product via a third reactor, the MX recycled to an input of the second region of the electrochemical cell;

contacting a first region of the electrochemical acidification cell having an cathode with a catholyte comprising water;

contacting a second region of the electrochemical acidification cell having an anode with an anolyte comprising HX;

contacting an acidification region of the electrochemical acidification cell with M-carboxylate;

applying an electrical potential between the anode and the cathode of the electrochemical acidification cell sufficient to produce the first product, a carboxylic acid, recoverable from the acidification region of the electrochemical acidification cell, a halogen recoverable from the second region of the electrochemical acidification cell, $H_2$ recoverable from the first region of the electrochemical acidification cell, and a caustic compound, the caustic compound recycled as an input to the third reactor.

17. The method according to claim 16, further comprising:
reacting the carboxylic acid and the $H_2$ from the electrochemical acidification cell in a thermal hydrogenation chamber to produce a third product.

18. The method according to claim 17, wherein the third product includes at least one of glyoxylic acid, glycolic acid, glyoxal, glycolaldeyde, ethylene glycol, ethanol, acetic acid, acetaldehyde, ethane, or ethylene.

19. The method according to claim 16, wherein the second product is at least one of an alcohol, an alkene, an alkyne, an aldehyde, a ketone, an alkane, and mixtures thereof.

20. The method according to claim 16, wherein the cathode and the anode of the electrochemical cell and the cathode and the anode of the electrochemical acidification cell are separated by at least one ion permeable barrier that operates at a temperature of less than 600 degrees C.

21. The method according to claim 20, wherein the at least one ion permeable barrier includes one of a polymeric or inorganic ceramic-based ion permeable barrier.

22. The method according to claim 16, wherein the catholyte of the electrochemical cell is liquid phase and the anolyte is gas phase.

23. The method according to claim 16, wherein the caustic compound is MOH.

24. A method for co-producing M-carboxylate and bromine, the method comprising the steps of:
contacting a first region of an electrochemical cell having a cathode with a catholyte comprising carbon dioxide;
contacting a second region of the electrochemical cell having an anode with an anolyte comprising an MBr where M is at least one cation;
applying an electrical potential between the anode and the cathode of the electrochemical cell sufficient to produce the M-carboxylate recoverable from the first region of the electrochemical cell and the bromine recoverable from the second region of the electrochemical cell;
reacting the bromine from the second region of the electrochemical cell with an alkane to produce a halogenated compound and HBr, the HBr being recycled back to an acidification chamber;
reacting the M-carboxylate with the HBr via the acidification chamber to produce a carboxylic acid and MBr, the MBr being recycled to an input of the second region of the electrochemical cell.

25. The method as claimed in claim 24, wherein the alkane is ethane.

26. The method as claimed in claim 25, wherein the halogenated compound is bromoethane.

27. The method as claimed in claim 26, wherein M is tetrabutylammonium.

* * * * *

UNITED STATES PATENT AND TRADEMARK OFFICE
CERTIFICATE OF CORRECTION

PATENT NO. : 8,692,019 B2  
APPLICATION NO. : 13/724807  
DATED : April 8, 2014  
INVENTOR(S) : Kyle Teamey and Jerry J. Kaczur Page 1 of 1

It is certified that error appears in the above-identified patent and that said Letters Patent is hereby corrected as shown below:

On the Title Page Item (12) Inventor Name should read, Teamey et al.

On the Title Page Item (72) Inventors should read, Kyle Teamey, Washington, DC (US); Jerry J. Kaczur, North Miami Beach, FL (US).

Signed and Sealed this  
Fifteenth Day of July, 2014

Michelle K. Lee  
*Deputy Director of the United States Patent and Trademark Office*